(12) United States Patent
Stien et al.

(10) Patent No.: US 9,198,722 B2
(45) Date of Patent: Dec. 1, 2015

(54) MEDICAL INSTRUMENT AND METHOD OF PERFORMING A SURGICAL PROCEDURE WITH THE MEDICAL INSTRUMENT

(71) Applicant: Stewart and Stien Enterprises, LLC, Eau Claire, WI (US)

(72) Inventors: Karl E. Stien, Eau Claire, WI (US); Nathaniel J. Stewart, Eau Claire, WI (US)

(73) Assignee: Stewart and Stien Enterprises, LLC, Eau Claire, WI (US)

( * ) Notice: Subject to any disclaimer, the term of this patent is extended or adjusted under 35 U.S.C. 154(b) by 275 days.

(21) Appl. No.: 13/889,561

(22) Filed: May 8, 2013

(65) Prior Publication Data

US 2013/0253510 A1 Sep. 26, 2013

Related U.S. Application Data

(63) Continuation-in-part of application No. 13/409,803, filed on Mar. 1, 2012, now Pat. No. 9,017,327.

(51) Int. Cl.
*A61B 18/18* (2006.01)
*A61B 18/14* (2006.01)
*A61B 18/00* (2006.01)

(52) U.S. Cl.
CPC ........... *A61B 18/1482* (2013.01); *A61B 18/148* (2013.01); *A61B 2018/00595* (2013.01); *A61B 2018/00601* (2013.01); *A61B 2018/1412* (2013.01); *A61B 2018/1422* (2013.01)

(58) Field of Classification Search
CPC ........... A61B 18/14; A61B 2018/1405; A61B 2018/141; A61B 2018/1412; A61B 2018/1422; A61B 18/1482; A61B 18/148; A61B 2018/00595; A61B 2018/00601

USPC ....................................................... 606/37, 39
See application file for complete search history.

(56) References Cited

U.S. PATENT DOCUMENTS

| | | | |
|---|---|---|---|
| 4,963,147 A | 10/1990 | Agee et al. | |
| 5,261,906 A | 11/1993 | Pennino et al. | |
| 5,354,296 A | 10/1994 | Turkel | |
| 5,360,428 A | 11/1994 | Hutchinson, Jr. | |
| 5,460,629 A | 10/1995 | Shlain et al. | |
| 5,849,011 A | 12/1998 | Jones | |
| 6,491,691 B1 | 12/2002 | Morley et al. | |
| 6,783,524 B2 | 8/2004 | Anderson et al. | |
| 6,808,525 B2 | 10/2004 | Latterell et al. | |
| 7,276,065 B2 | 10/2007 | Morley et al. | |
| 7,402,162 B2 * | 7/2008 | Ouchi | 606/45 |
| 7,824,398 B2 | 11/2010 | Woloszko et al. | |
| 2008/0312652 A1 * | 12/2008 | Bell et al. | 606/48 |
| 2009/0125038 A1 * | 5/2009 | Ewers et al. | 606/142 |

* cited by examiner

*Primary Examiner* — Christopher D Koharski
*Assistant Examiner* — Michael Carey
(74) *Attorney, Agent, or Firm* — Wood, Phillips, Katz, Clark & Mortimer

(57) ABSTRACT

A medical instrument having an elongate frame with proximal and distal ends. An operating assembly is at a proximal region of the frame with a working assembly at a distal region of the frame. The working assembly has a tip with a leading free end to be engaged with a human body at an operation site. The working assembly has at least one cautery component that: a) contacts a human body at the cutting location; and b) is operable to generate a current that alters a contacted portion of the human body at the cutting location. An insulating material is located at least one of: i) at the leading free end; and ii) between the at least one cautery component and the leading free end so that current does not conduct from the at least one cautery component to body tissue during a medical procedure.

24 Claims, 7 Drawing Sheets

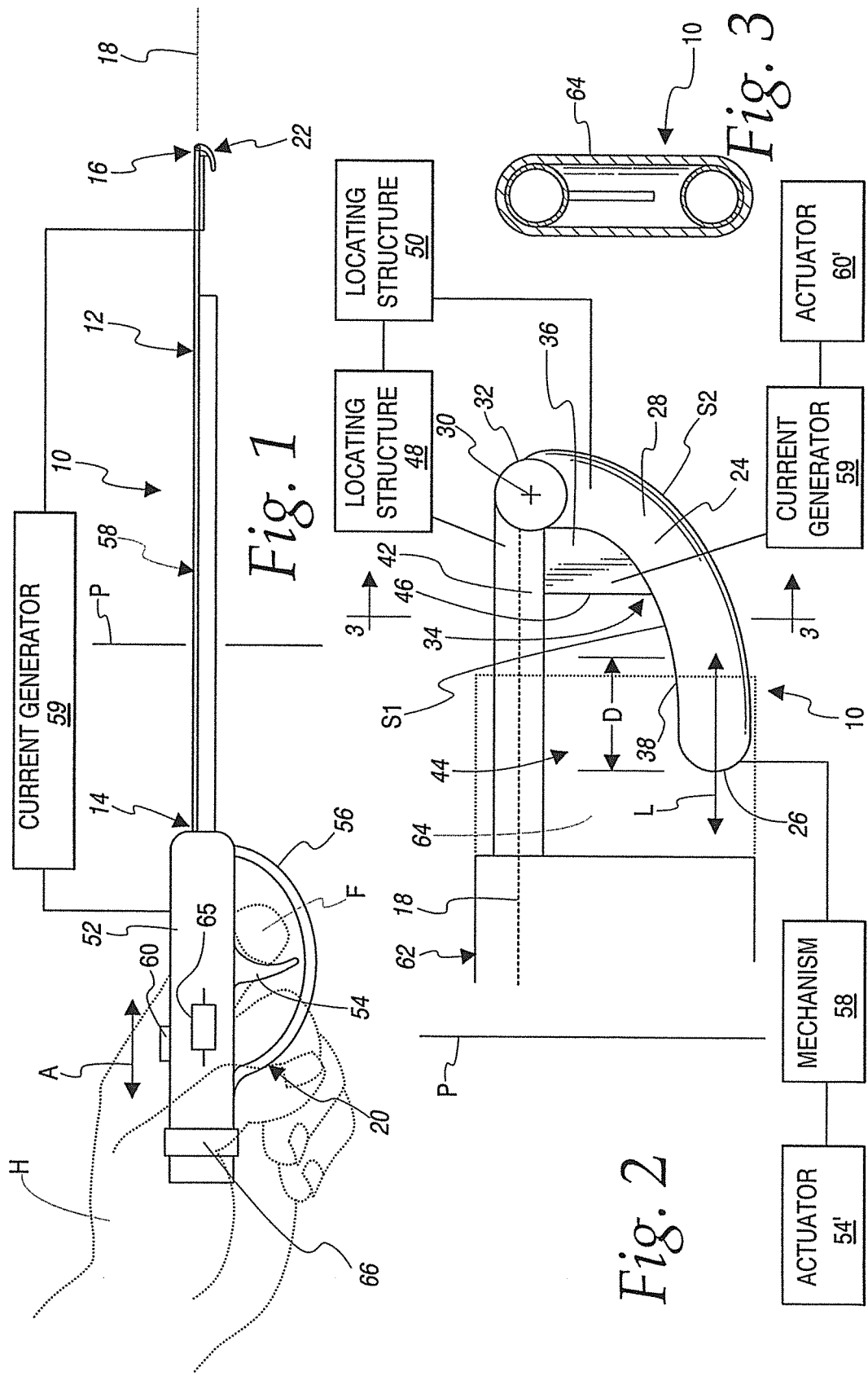

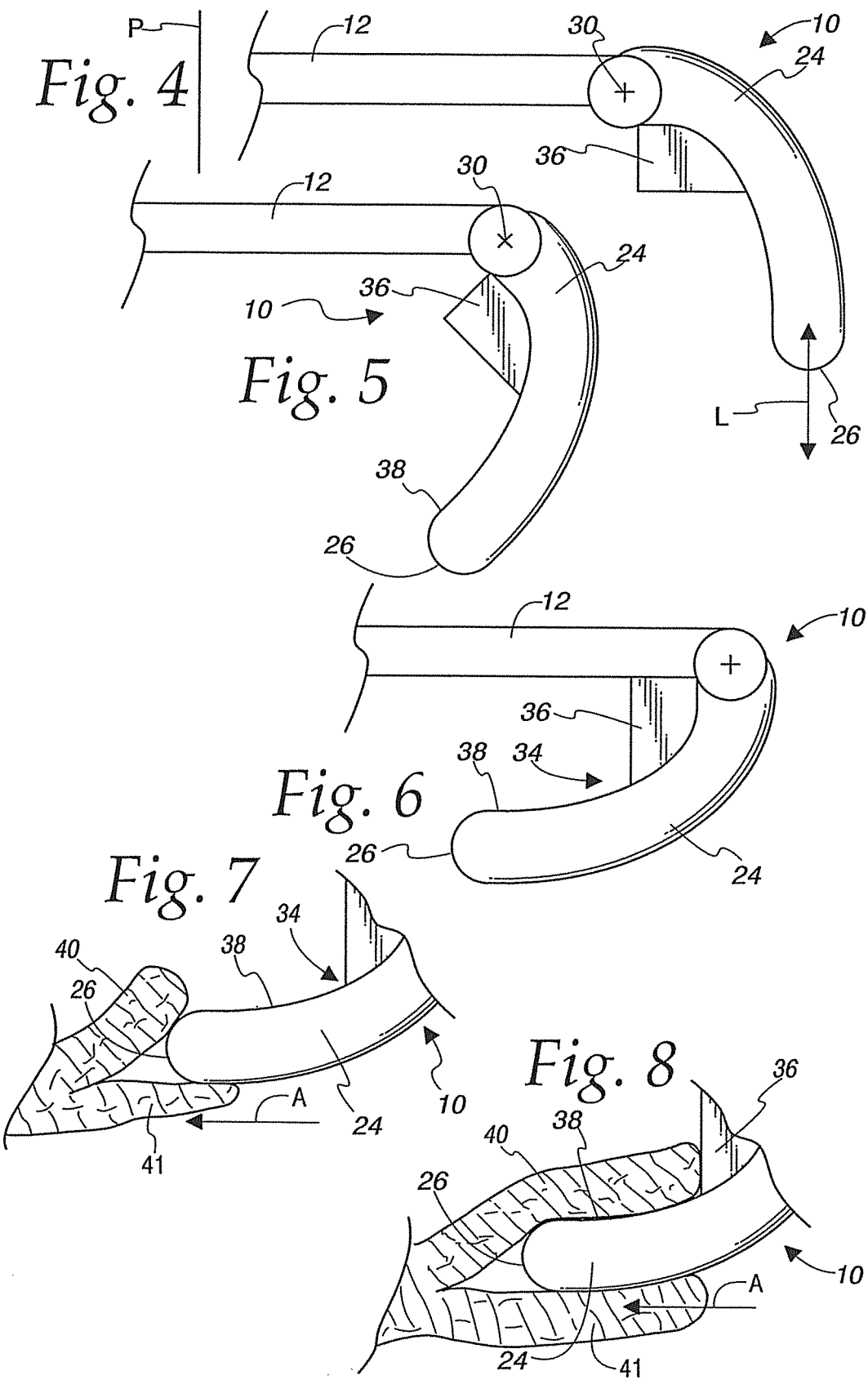

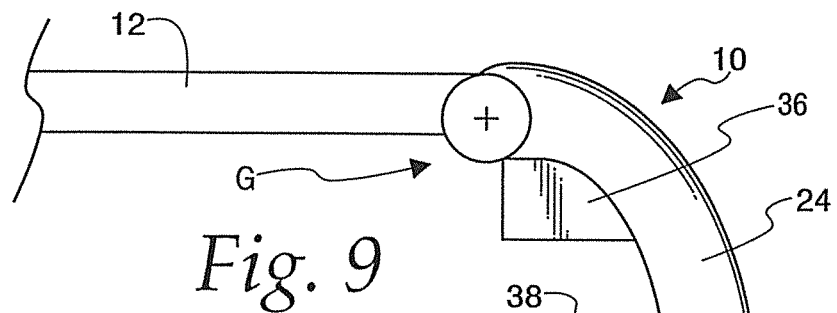
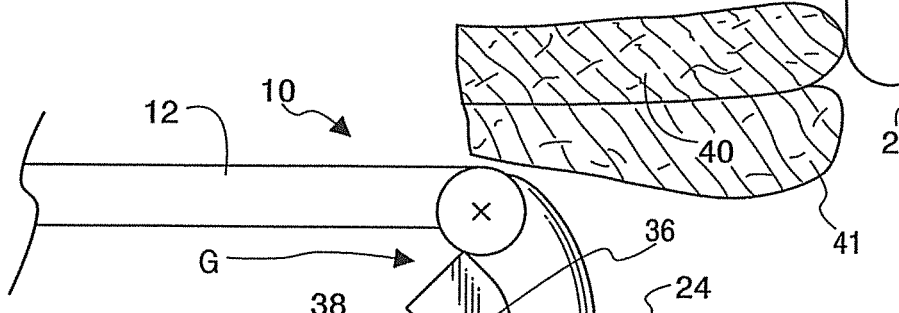
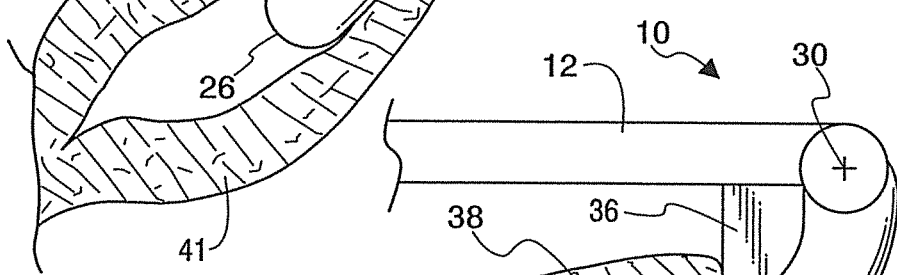

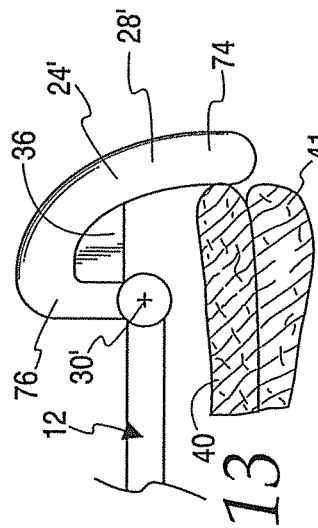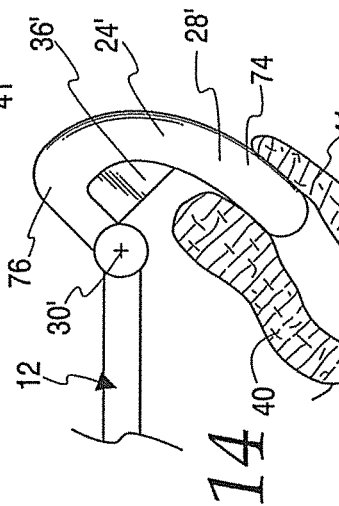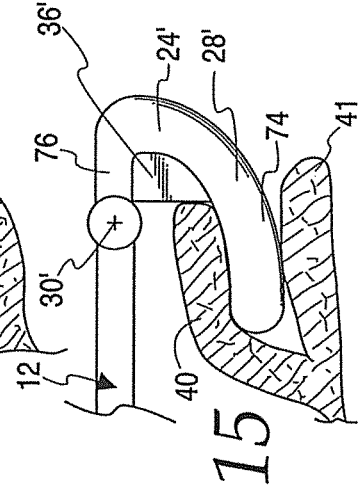
Fig. 13　　　Fig. 14　　　Fig. 15
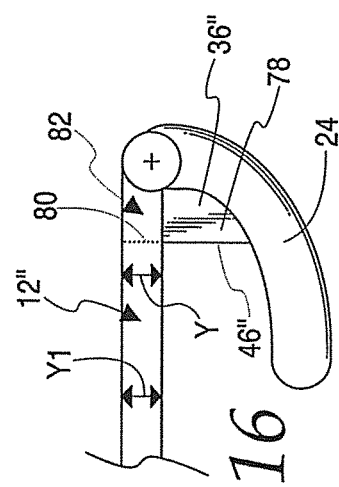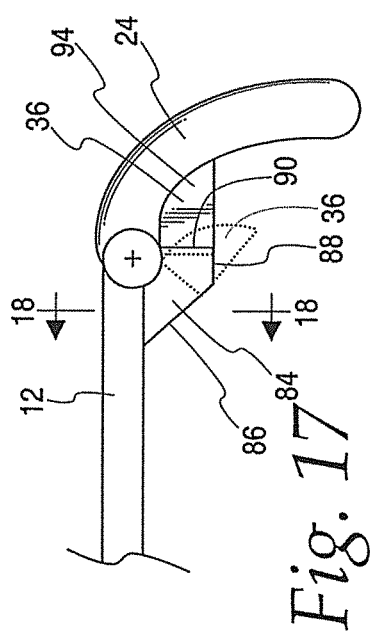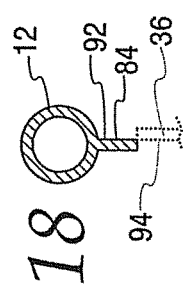
Fig. 16　　　Fig. 17　　　Fig. 18

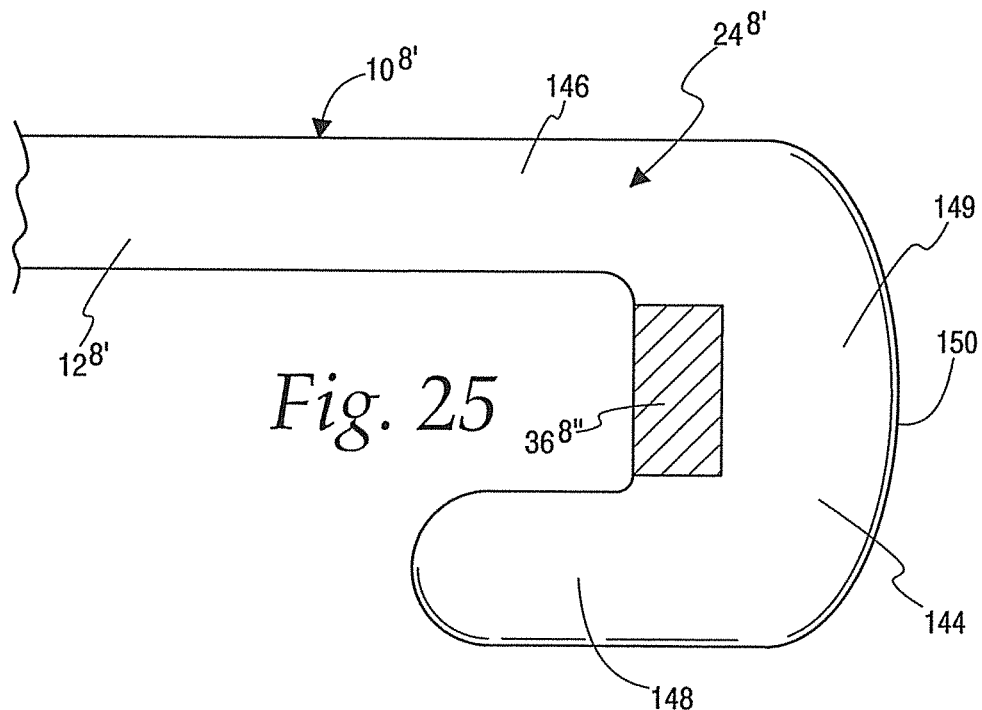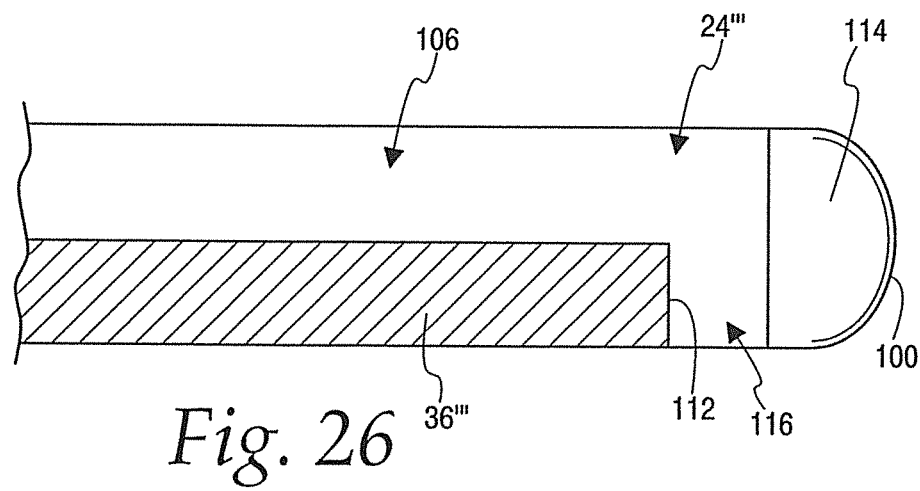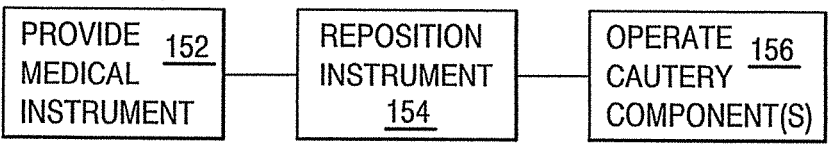

MEDICAL INSTRUMENT AND METHOD OF PERFORMING A SURGICAL PROCEDURE WITH THE MEDICAL INSTRUMENT

BACKGROUND OF THE INVENTION

1. Field of the Invention

This invention relates to medical instruments and, more particularly, to a medical instrument for repositioning human body tissue at an operation site preparatory to cauterization. The invention is also directed to a method of using such a medical instrument.

2. Background Art

In many surgical procedures, tissue is required to be controllably dissected. This dissection is commonly effected using cauterization. Care must always be taken to avoid collateral tissue damage when cauterization is performed.

It is known to use a medical instrument having a repositionable metal tip with an associated cautery device. The tip is controlled to strategically reposition the tissue so that it can be cauterized. Since the cautery device is not electrically isolated from the metal tip, even if care is taken, some collateral tissue damage is likely to occur.

Further, conventional tips are typically configured so that they are at least nominally aligned with the length of an elongate frame that extends between a proximal end, at which the instrument is controlled, and a distal end, at which the tip is provided. An exemplary configuration for this type of device is shown in U.S. Pat. No. 5,360,428, to Hutchinson, Jr. A substantial amount of skill is required to effectively orient the device and balance the tissue to be cauterized on the tip so that the tissue will be contacted precisely where desired by the cautery components and dissected in the desired plane.

Further, Hutchinson, Jr. has limitations in terms of the angle at which the line of the projecting tip is disposed relative to the tissue as the procedure is initiated. Devices exist where tips, such as that in Hutchinson, Jr., have a slight curvature. However, this may not eliminate this problem. A surgeon may still have difficulty repositioning tissue and dissecting it in a required plane. Contending with this problem may undesirably lengthen procedure time.

As one example, this type of instrument is commonly used in arthroscopic hip capsulotomies. With conventional instrumentation, it is difficult for the surgeon to pull the capsule away from the femoral head prior to cutting the capsule, particularly in a plane parallel to the femoral neck. There is a significant risk of collateral damage to the underlying femoral cartilage by the cautery device. Taking the steps and care necessary to minimize this collateral damage potentially increases the time to perform the procedure beyond what is optimally desired and efficient.

SUMMARY OF THE INVENTION

In one form, the invention is directed to a medical instrument having an elongate frame with proximal and distal ends. An operating assembly is at a proximal region of the frame with a working assembly at a distal region of the frame. The working assembly has a tip with a leading free end to be engaged with a human body at an operation site. The working assembly has at least one cautery component that: a) contacts a human body part at the cutting location; and b) is operable to generate a current that alters a contacted portion of the human body part at the cutting location. An insulating material that is not electrically conductive is located at least one of: i) at the leading free end; and ii) between the at least one cautery component and the leading free end so that current does not conduct from the at least one cautery component to the leading free end to human body tissue during a medical procedure.

In one form, the insulating material is at the leading free end.

In one form, the elongate frame and tip are substantially straight from a proximal region of the elongate frame fully to the leading free end.

In one form, the tip defines in conjunction with a part of the elongate frame an "L" shape.

In one form, the tip defines in conjunction with a part of the elongate frame a "J" shape.

In one form, the "J" shape is defined by a base and spaced legs. The base has an exposed surface defining a distalmost part of the medical instrument. Insulating material that is not electrically conductive is located at least one of: a) at the exposed surface on the base; and b) between the at least one cautery component and the exposed surface on the base so that current does not conduct from the at least one cautery component to the exposed surface on the base to human body tissue during a medical procedure.

In one form, the tip has an orientation that is at all times fixed.

In one form, the tip can be selectively reoriented relative to the frame through the working assembly.

In one form, the at least one cautery component has an edge that engages the human body part at the cutting location and the edge is one of: a) substantially straight; and b) defined by two substantially straight lengths that are angled with respect to each other.

In one form, the insulating material is one of: a) a plastic; and b) a non-metal material.

In one form, the at least one cautery component is an edge on a cylindrical portion of the medical instrument and the insulating material is provided on the cylindrical portion of the medical instrument at a location diametrically opposite to the edge.

In one form, the tip has an exposed outer surface area. The at least one cautery component has a blade with an exposed portion making up a part of the exposed surface area. Substantially the entirety of the exposed surface area, with the exception of the exposed portion of the blade, is made from the insulating material.

In one form, the leading free end is convexly curved.

In one form, the "L" shape is defined by angled legs. One of the angled legs has a convex surface defining a distalmost part of the medical instrument.

In one form, the leading free end is convexly curved.

In one form, the at least one cautery component has a blade that is provided on the base of the "J".

In one form, the at least one cautery component has a blade and the insulating material extends radially outwardly from the central axis of the frame beyond the blade.

In one form, the invention is directed to a method of performing a surgical procedure. The method includes the steps of: providing a medical instrument as described above; repositioning the medical instrument so that the distal end of the medical instrument is moved up to and into contact with a human body part at a cutting location; and operating the at least one cautery component to alter the contacted human body part at the cutting location through the generated current.

In one form, the method further includes the step of repositioning a portion of the contacted human body part by bearing the insulating material against the portion of the human body part.

In one form, the surgical procedure is carried out while maintaining the tip at all times in a fixed orientation.

BRIEF DESCRIPTION OF THE DRAWINGS

FIG. 1 is a side elevation view of one form of medical instrument, according to the present invention, and made up of an elongate frame with operating and working assemblies, respectively at proximal and distal regions thereof;

FIG. 2 is an enlarged, fragmentary, elevation view of the working assembly on the medical instrument in FIG. 1, and a repositionable tip thereon, with the tip in a first position;

FIG. 3 is a cross-sectional view of the working assembly taken along line 3-3 of FIG. 2;

FIG. 4 is an enlarged, fragmentary, elevation view of the medical instrument, as in FIG. 2, and showing the tip in a second position;

FIG. 5 is a view as in FIG. 4 with the tip moved to another position between the first and second positions;

FIG. 6 is a view as in FIGS. 4 and 5 with the tip moved from the second position to and past the FIG. 5 position to the first position, as shown also in FIG. 2;

FIG. 7 is an enlarged, fragmentary, elevation view of the medical instrument showing the tip engaging a tissue portion preparatory to cauterization with the tip in the first position, shown in FIGS. 2 and 6;

FIG. 8 is a view as in FIG. 7 wherein the tip and tissue portion have been relatively moved to place the tissue portion at a cutting location against a cautery device on the working assembly while maintaining the tip in the first position;

FIG. 9 is a view as in FIGS. 7 and 8 wherein the tip is placed in the second position upon initially engaging a tissue portion;

FIG. 10 is a view as in FIG. 9 wherein the tip is repositioned to guide the tissue portion towards the cutting location;

FIG. 11 is a view as in FIGS. 9 and 10 wherein the tip is moved to the first position whereby the tissue portion is moved fully to the cutting location;

FIG. 12 is a flow diagram representation of a method of performing a surgical procedure according to the present invention;

FIGS. 13-15 are views corresponding successively to FIGS. 9-11 and showing a modified form of working assembly, according to the present invention;

FIG. 16 is a view as in FIG. 11 and showing a modified form of cautery component on the working assembly;

FIG. 17 is a view as in FIG. 9 and showing a modified form of working assembly including a wall that cooperates with a cautery component as the tip thereon is moved over its permissible range;

FIG. 18 is a cross-sectional view of the working assembly taken along line 18-18 of FIG. 17;

FIG. 25 is a view as in FIG. 24 of a still further modified form of medical instrument, according to the invention;

FIG. 26 is a fragmentary view showing a leading end of the medical instrument of FIG. 20 with a modification thereto; and FIG. 27 is a flow diagram representation of a method of performing a surgical procedure according to the present invention and utilizing the medical instruments as shown, for example, in FIGS. 19-26.

DETAILED DESCRIPTION OF THE PREFERRED EMBODIMENT

Figure 19:
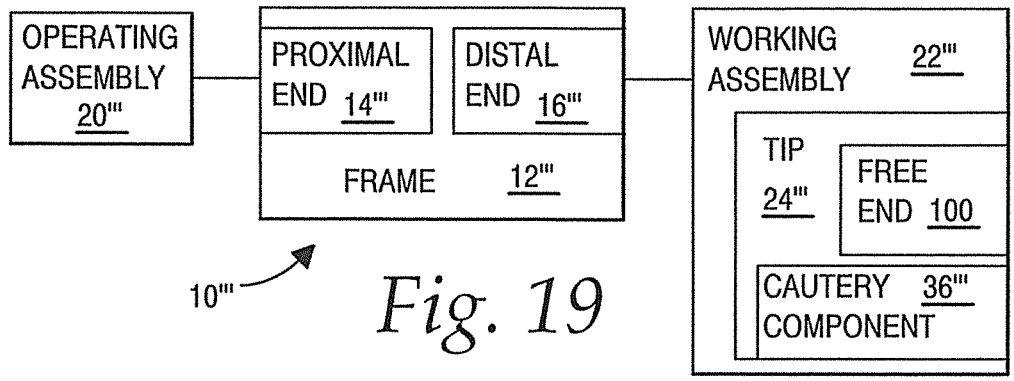
FIG. 19 is a schematic representation of another form of medical instrument, according to the invention.

In FIGS. 1-11, a medical instrument, according to the present invention, is shown at 10. The medical instrument 10 consists of an elongate frame 12 with proximal and distal ends 14, 16, respectively, spaced in a lengthwise direction along a central axis 18 of the frame 12.

An operating assembly 20 is provided at a proximal region of the frame 12. A working assembly 22 is provided at a distal region of the frame 12.

The working assembly 22 consists of a cantilevered tip 24 with a free end 26. The tip 24 has a body 28. The working assembly 22 is reconfigurable by an operator through the operating assembly 20 by selectively reorienting the tip 24 relative to the frame 12. In the depicted embodiment, the tip body 28 is movable relative to the frame 12 around a fixed axis 30.

The various contemplated positions for the tip 24 can also be clearly described relative to a reference plane P that extends through the frame 12 orthogonally to the central axis 18 at a location on the frame 12 spaced axially from the working assembly 22 toward the operating assembly 20. The location of the reference plane P in FIG. 1 is not limited to what is shown.

The body 28 of the tip 24 has a continuously curved shape between the rounded free end 26 and axis 30. The body 28 may be locally narrowed between the free end 26 and axis 30, as shown in dotted lines in FIG. 2, for reasons explained below. While the body 28 has a continuous curve, for purposes of the description and claims herein, the tip 24 will be characterized as "projecting" in a direction that is substantially along a line L, indicated by the double-headed arrow in FIGS. 2 and 4, which is generally parallel to a discrete length of the body 28 extending from the free end 26 a distance D towards the opposite body end 32.

The tip 24 is movable in a range between a first position, as shown in FIG. 2, and a second position, as shown in FIG. 4. The actual range could be less than that shown or greater than that shown, but is preferably selected so that the tip 24 can be placed in at least the first and second positions depicted.

In one position within this range, which is shown in the exemplary form as the first position, the tip 24 projects in a first axial direction toward the reference plane P to allow the tip free end 26 to be engaged, as with a tissue portion at an operation site, and controllably moved through the instrument guidingly along the tip to a cutting location at 34.

The medical instrument 10 is designed to manipulate and dissect tissue and other potentially human body parts. For purpose of the detailed description and claims, "body part" will be used to encompass any part of the human body that can be engaged by the medical instrument, with the depicted or like configuration, so that a portion thereof can be situated at the cutting location 34 whereat it can be dissected, as described below.

At the cutting location 34, at least one cautery component 36 is provided. In this embodiment, there is a single cautery component 36. The cautery component 36 contacts the body part at the cutting location 34 and is operable to generate a current that heats a contacted portion of the human body part at the cutting location 34.

By reason of the shape of the tip body 28, the instrument 10 can be manipulated so as to readily and consistently place a portion of the subject body part predictably at the cutting location 34 in an orientation to dissect across a desired cutting plane. More specifically, the tip body 28 has a surface portion 38 that curves progressively from the convex/rounded tip free end 26 up to the cutting location at 34. With the dotted line configuration of FIG. 2, the body 28 is slightly bulbous adjacent to the free end and tapers in diameter away therefrom so as not to inhibit guided sliding movement of a body part portion therealong. The surface portion 38 is also slightly concavely curved over this body length to facilitate this sliding movement of the portion of the body part thereagainst.

As seen in FIGS. 7 and 8, as the tip 24 encounters a body part portion 40, such as tissue, at the operation site, advancement of the instrument 10 in the direction of the arrow A causes the portion 40 to be drawn upwardly, as away from bone and/or another body part portion 41 at the operation site, and move guidingly up the free end 26 to the surface portion 38. Continued advancement of the instrument 10 in the direction of the arrow A causes the portion 40 to arrive at the cutting location 34, whereat it encounters the cautery component 36. In FIGS. 7 and 8, the tip 24 is in the first position therefor, as shown in FIGS. 2 and 6, though the same steps can be performed with the tip 24 in other positions.

The body 28 is preferably made from a material that is not electrically conductive, such as a plastic or other non-metal material, over those surface portions, as shown at S1, S2, that are exposed to potentially contact tissue during procedures. The entire body 28 may be made to be non-conductive. Ideally, as the instrument 10 engages body parts during a procedure, the surfaces on the instrument 10 that contact the body parts will not conduct electricity with the cautery component 36 energized. This minimizes the inadvertent infliction of any damage upon any body tissue or other body part other than the body part intended to be contacted by the cautery component 36. Thus, during cauterization, surrounding tissue can be insulated from the cautery component 36 to thereby minimize collateral damage inflicted by heat generated by the energized cautery component 36.

In this embodiment, a distal portion 42 of the frame 12 and the tip body 28 cooperatively define a "U" shape opening axially in a first direction toward the operating assembly 20. With this arrangement, pressure application upon the instrument 10 in the first axial direction causes the body part portion 40 to become captively blocked in a space at 44. The frame portion 42 and tip 24 define spaced legs of the "U" bounding that space 44. The width of the space 44 narrows slightly towards the cutting location with the tip 24 in its first position so that the body part portion 40 is consistently funneled to against the cautery component 36. So long as pressure is maintained on the instrument 10 in the direction of the arrow A, the body part portion 40 will not escape from the space 44.

Additionally, the distal portion 42 of the frame 12 can be made with a non-conductive material to be even more certain that no damage will be inflicted upon the body part portion 40 other than at the intended cauterization site. With this construction, the entire "U" shape on the working assembly 22 is electrically insulated as it engages surrounding body parts as the cautery component 36 is brought into contact with a body part region to be cauterized. The cauterization component 36 may be made, as shown, to span between the frame portion 42 and tip 24 to be consistently brought into contact with the body part portion 40 in a desired plane. In the embodiment shown, the cautery component 36 defines a substantially straight edge 46 that engages the body part portion 40 at the cutting location 34. The edge 46 is shown to extend fully and continuously between the tip 24 and frame portion 42. While the edge 46 is shown as straight, this is not a requirement, nor is it a requirement that there be a single component that produces the cauterization energy. Further, the edge 46 need not be continuous as shown.

The process of dissecting the particular body part portion 40 may be initiated with the tip 24 in the first position therefor, as shown in FIG. 6, wherein the line of the tip 24 is substantially parallel to, and spaced radially from, the frame axis 18. Alternatively, the angle of projection of the tip 24 can be changed depending upon the particular application and geometry at the operation site. For example, the projecting line L of the tip 24 may be as shown in FIGS. 4 and 9, representing the aforementioned second position, wherein the tip projecting line is substantially parallel to the reference plane P. The cauterization process could be carried out with this tip position maintained. Alternatively, the tip 24 might be repositioned to a third position, as shown in FIGS. 5 and 10 or back into the first position in FIGS. 4 and 9. As the position of the tip 24 changes, the body part portion 40 is guidingly slid along the surface portion 38 to against the edge 46 at the cutting location 34.

Referring to FIGS. 9-11, with the tip 24 initially in the FIG. 9 position, the free end 26 can be situated at the interface between the body part portions 40, 41. Movement of the tip 24 toward the FIG. 11 position wedges the body part portion 40 away from the body part portion 41, as seen in FIG. 10, until the body part portion 40 is eventually situated to engage the cautery component 36, as seen in FIG. 11.

By reason of making exposed surfaces on the tip 24 non-conductive, the body part portion 41 remains at all times electrically insulated from the cautery component 36.

Cooperating locating structure, shown schematically at 48, 50, may be provided respectively on the frame 12 and tip 24 to allow the first and second positions, and potentially the third and other desired tip positions, to be consistently set and releasably maintained. The cooperating locating structure 48, 50 may be a detent-type of arrangement or take the form of another type of component known to those skilled in the art, or devisable thereby.

The operating assembly 20 is shown to include a graspable handle portion 52 around which a surgeon's fingers can be wrapped to firmly hold the instrument 10 and allow comfortable manipulation thereof. A trigger/actuator 54 is shown in FIG. 1 and is engageable and movable, as in the direction of the arrow AA, by a finger F on the hand H that is wrapped around the graspable handle portion 52 to controllably reposition the tip 24. A U-shaped, protective cage 56 shields the trigger region and the fingers that operate the trigger 54, thereby avoiding an inadvertent contact that might cause an unintended movement of the trigger 54 by the surgeon during a procedure.

A mechanism is shown at 58, partially within the frame 12, for converting movement of the trigger 54 into a force that causes pivoting of the tip 24. Many different suitable mechanisms 58 could be devised by one skilled in the art. Thus there is no need herein to discuss details of such structure.

The invention also contemplates other types of actuators for the mechanism 58, as shown generically at 54' in FIG. 2.

The cautery component 36 is energized by a current generator 59 of conventional construction. The current generator 59 is operable by a switch actuator 60 that is translatable along the line of the double-headed arrow AA between "on" and "off" positions and potentially to vary operating current.

The current generator 59 can be operated through other types of actuators. A generic actuator 60' is shown in FIG. 2 and may be in the form of a foot pedal or other type of mechanism.

Another optional feature is the provision of a cover assembly at 62. The cover assembly 62 consists of a sleeve 64 with a generally oval cross-sectional shape, as shown in FIG. 3, to slide over a portion of the tip 24, with the tip 24 in its first position and the cover assembly 62 in a covering state. The sleeve 64 can be retracted to the solid line position in FIGS. 1 and 2 into a retracted state wherein the tip 24 is fully exposed. The sleeve 64 can be repositioned through an actuator 65 on the handle 52. The actuator 65 is shown as a translatable component engageable and movable by the thumb or a finger on a user's hand H, as along a line indicated by the double-headed arrow AA.

By extending fully around the free end 26 of the tip 24 with the tip 24 in its first position, the direction of the working assembly 22 to the operating site, and withdrawal of the same therefrom, is facilitated without snagging of the tip free end 26, whether the procedure is carried out laparoscopically or through an open incision.

An actuator 66 is shown in FIG. 1 in the form of a ring that is journaled for turning relative to the graspable handle 52 about an axis. This actuator 66 design might be used instead of, or in conjunction with, actuators as previously described for the tip 24, the current generator 59 and the cover assembly 62.

With the medical instrument 10 as depicted, a method of performing a surgical procedure can be carried out as shown in flow diagram form in FIG. 12.

As shown at block 67, a medical instrument is provided, as described above.

As shown at block 68, the tip is engaged with a body part.

As shown in block 70, the tip is repositioned relative to the portion of the body part by: a) moving the medical instrument relative to the body part; and/or b) repositioning the tip relative to the frame from one position into another position to thereby cause a portion of a human body part to move guidingly along the tip from the free end to the cutting location whereat the portion of the human body part engages the at least one cautery component.

As shown at block 72, the one cautery component is operated to dissect the portion of the body part at the cutting location.

As noted previously, the procedure can be carried out as shown in FIGS. 7 and 8 with the tip engaged and repositioned relative to the body part portion without changing the position of the tip relative to the frame. Alternatively, as shown sequentially in FIGS. 9-11, the tip can be reoriented to effect engagement and repositioning of the body part therealong to present the body part portion at the cutting location. In both cases, the portion of the body part is lifted by, and slid along, the tip.

With the tip 24 positioned as in FIGS. 9 and 10, a gap G is produced that potentially could result in a body part being pinched between the cautery component 36 and frame 12 as the tip 24 moves further towards the FIG. 11 position and ultimately into the FIG. 11 position. While this gap G does not necessarily present a problem, the gap G can be eliminated by modifying the tip configuration.

In one modified form, as shown in FIGS. 13-15, a tip 24' is shown with a body 28' having a fixed "U" shape. One leg 74 of the "U" shape defined by the body 28' corresponds to the tip 24, previously described. The other leg 76 is connected to the frame 12 for guided pivoting movement around an axis 30'.

The body 28' is movable between the positions shown in FIGS. 13 and 15, causing the leg 74 to move correspondingly to the tip 24 between the FIG. 4 and FIG. 6 positions.

With the fixed "U" shape, the cautery component 36' is in fixed relationship to, and spans fully between, the legs 74, 76 throughout the range of movement of the body 28'.

As seen in FIGS. 13-15, the leg 74, which becomes a cantilevered "tip", cooperates with the aforementioned body part portions 40, 41 as it is moved between the FIGS. 13 and 15 positions, in the same manner that the tip 24 cooperates with the body part portions 40, 41, as it moves between the FIGS. 9 and 11 positions.

As a further alternative, as shown in FIG. 16, the tip 24 can be used with a modified form of frame 12" and cautery component 36".

The cautery component 36" has a body 78 and a cutting edge 46" thereon with an extended length Y compared to the cautery component 36. The frame 12" has a slot 80 formed therein to accept the extended portion at 82 of the cautery component 36".

Depending upon the dimension Y1 of the frame 12", the aforementioned gap G may be reduced or altogether eliminated using this configuration.

A still further alternative design is shown in FIGS. 17 and 18. In these Figures, the tip 24, frame 12, and cautery component 36, as described above, are utilized.

A wall 84 is fixed to the frame 12. The wall 84 is generally flat and bounded by straight edges 86, 88, 90 where the wall 84 projects from the frame 12. The plane of one surface 92 of the wall 84 is slightly offset and parallel to a flat surface 94 on the cautery component 36.

The wall 84 may be configured so that the wall 84 and cautery component 36 slide one against the other into different overlapping relationships as the tip 24 is pivoted, thereby to cooperatively span between the tip 24 and frame 12 at all times as the tip 24 is repositioned. Depending upon how the parts are configured, the aforementioned gap G can be either partially or fully eliminated.

Referring now to FIG. 19, there is a generic showing of a modified form of medical instrument 10''', with specific embodiments thereof shown in FIGS. 20-26. The medical instrument 10''' consists of an elongate frame 12' with proximal and distal ends 14''', 16''', respectively. An operating assembly 20''' is provided at a proximal region of the frame 12''', with a working assembly 22''' at a distal region thereof. The medical instrument 10''' differs primarily from those constructions previously described by reason of the fact that the working assembly 22''' has an associated tip 24''' that need not be reconfigurable, although reconfiguration is contemplated. As such, the tip 24''' may essentially be integral with the frame 12''' but, for purposes herein, will be considered to be a separate component. The tip 24''' has a leading free end 100 to be engaged with a human body at an operation site.

The precise construction of the operating assembly 20''' is not critical to the invention. Myriad different designs thereof could be devised by those skilled in this art.

The working assembly 22''' includes at least one cautery component 36''' that may be on, or adjacent to, the tip 24'''. In FIG. 19, the cautery component 36''' is shown as part of the tip 24'''; however, this is not a requirement.

The basic layout and operation of components for the medical instrument 10''' is the same as that for their counterparts in the previously described medical instruments 10, 10', 10''. Thus, it is not necessary to re-describe these basic components and their relationships. It suffices to say that on the working assembly 22''', at least one cautery component 36''': a) contacts a human body part at a cutting location; and b) is operable to generate a current that alters a contacted portion of the human body at the cutting location.

Figure 20:
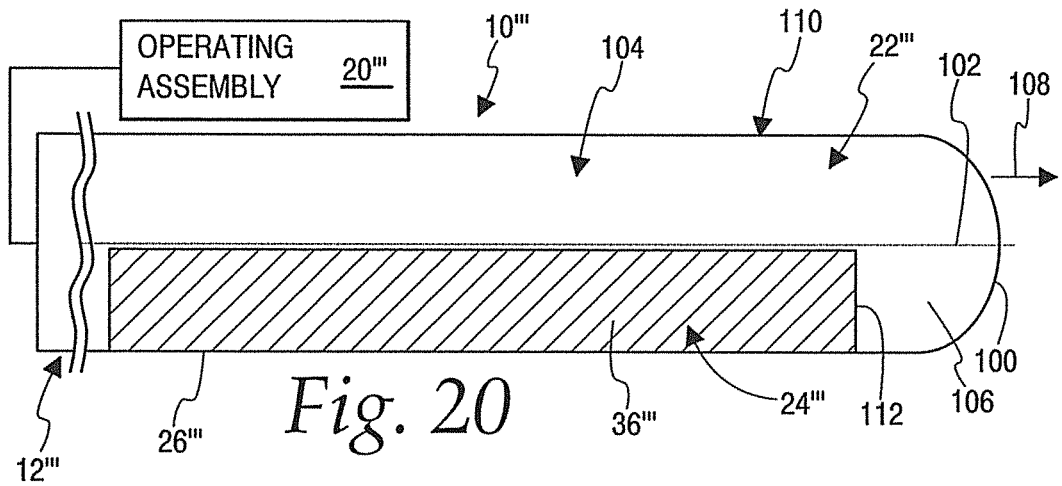
FIG. 20 is a fragmentary, elevation view of one specific form of medical instrument as depicted in FIG. 19.

One specific form of the medical instrument 10''' is shown in FIG. 20. The medical instrument 10''' has a frame 12''' with an associated operating assembly 20''', shown in schematic form, and a working assembly 22''' incorporating a tip 24'''.

The tip 24''' incorporates the cautery component 36''', in this case in the form of an elongate blade with a substantially straight operating edge 26''' with the line thereof extending generally parallel to a central axis 102 of the frame 12'''.

According to the invention, insulating material defines substantially the entire exposed surface 104 of the tip 24''', with the exception of that portion of the exposed surface area defined by the blade 36''' as required for it to be operational. The insulating material preferably makes up at least that portion of the tip 24''', and potentially the frame 12''', that become exposed to bodily tissue during a procedure. Conductive materials contiguous with, or in the vicinity of, the cautery component 36''' could conduct its generated current, directly or through bodily fluids, to surrounding tissues so as to potentially cause damage thereto. The insulating material provides an electrical barrier to inhibit such current conducting as might damage tissue, during introduction and/or while operating, the instrument 10'''.

In this embodiment, the tip 24''' has a body 106 that is generally cylindrical in cross-section with its axis coincident with the axis 102. As a result, the elongate frame 12''' and tip 24''' are substantially straight from a proximal region of the frame 12''' fully to the leading free end 100, in this case formed on the tip 24'''.

In this embodiment, substantially the entire area of the exposed surface 104 of the tip body 106, excluding the cautery component 36''', is made from the insulating material. As a result, as the medical instrument 10''' is introduced to a body cavity, as by movement in the direction of the arrow 108, the insulating material at the leading free end 100 will contact tissue and guide entry of the trailing portion of the medical instrument 10'''. The leading free end 100 is convex to facilitate this action.

Additionally with this construction, the insulating material makes up the portion of the body 106 at 110 that is diametrically opposite to the location of the edge 26'''. This portion 110 can be used to engage and reposition tissues to strategically situate the medical instrument 10''' preparatory to cauterization, without significant exposure of the tissue to the cautery component 36''', which may be activated as this movement occurs.

Further electrical insulation is achieved by situating the forward end 112 of the cautery component 36''' at a location spaced rearwardly from the leading free end 100.

While it is preferred to make the entire area of the exposed surface 104, excluding that made up by the cautery component 36''', of the insulating material, as an alternative, the insulating material can be more strategically utilized. For example, as shown in FIG. 26, the distal end of the body 106 made from insulating material may be capped with a conductive component 114 that defines the leading free end 100. With this arrangement, there is a region at 116 that electrically isolates the end 112 of the cautery component 36''' from the component 114. Thus, the same insulating effect is realized by placing the insulating material between the cautery component 36' and the leading free end 100. As a result, current does not conduct from the cautery component 36''' to the leading free end 100 such that it might additionally conduct therethrough to body tissue during a medical procedure.

As noted previously, the tip 24''' is at all times fixed relative to the frame 12''' with this particular embodiment. It is conceivable that structure could be incorporated, such as that previously described or other structure, to allow reorientation of the tip 24'''.

As previously described, the nature of the insulating material is not critical to the present invention. As examples, the insulating material might be a plastic or other non-metal material, such as a composite, etc. The material is chosen so as not to freely conduct the current in a manner that could potentially damage contacted tissue.

Figure 21:
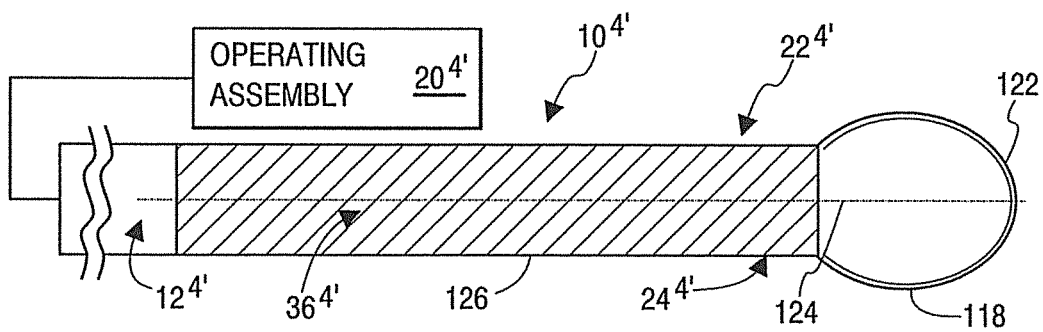
FIG. 21 is a view as in FIG. 20 of a further modified form of medical instrument, according to the invention.

In FIG. 21, a further modified form of medical instrument is shown at $10^{4'}$. The medical instrument $10^{4'}$ has a frame $12^{4'}$ with a working assembly at $22^{4'}$ at a distal region of the frame $12^{4'}$. An operating assembly $20^{4'}$ is incorporated at a proximal region of the frame $12^{4'}$.

In this embodiment, the working assembly $22^{4'}$ includes a tip $24^{4'}$ with a cautery component $36^{4'}$. The cautery component $36^{4'}$ is fully exposed around the circumference of the tip $24^{4'}$. At the distal end of the cautery component $36^{4'}$, another component 118 is incorporated into the tip $24^{4'}$ and is constructed so that its exposed, external peripheral surface 124 is made from an insulating material. The component 118 has a convex leading free end 122. The component 118 extends radially relative to a central axis 124 for the frame $12^{4'}$ and tip $24^{4'}$ beyond the circumferential surface 126 of the cautery component $36^{4'}$.

Figure 22:
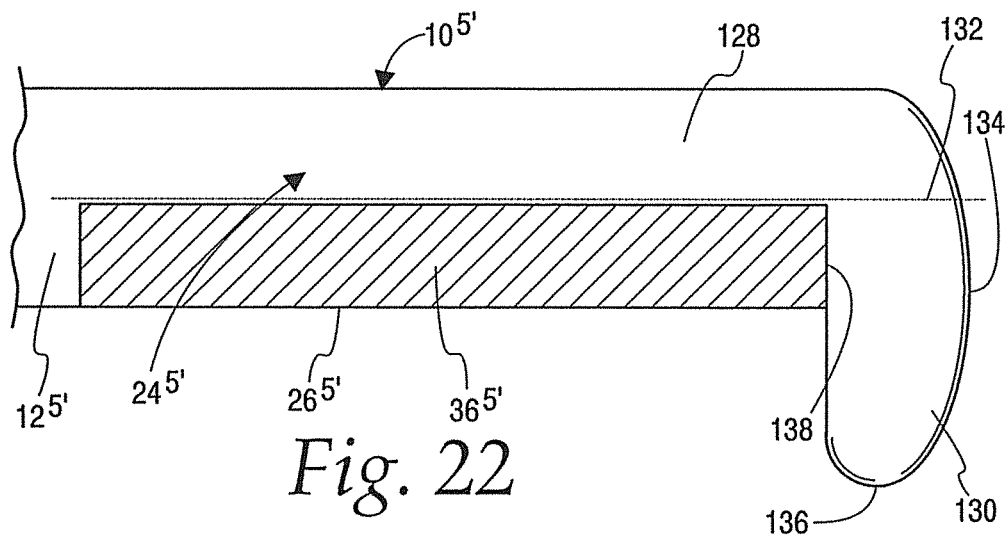
FIG. 22 is a view as in FIG. 21 of a further modified form of medical instrument, according to the invention.

In FIG. 22, a portion of a further modified form of medical instrument, according to the present invention, is shown at $10^{5'}$. In this embodiment, a tip $24^{5'}$ defines by itself and/or with a part of an elongate frame $12^{5'}$, an overall "L" shape. The "L" shape is defined by angled legs 128, 130, with the leg 128 having a length aligned with the central axis 132 of the frame $12^{5'}$.

The leg 130 has separate convex surfaces 134, 136 defining essentially separate leading free ends. The convex surface 134 defines the distalmost part of the medical instrument $10^{5'}$.

In this embodiment, the cautery component $36^{5'}$ has a straight edge $26^{5'}$ extending generally parallel to the axis 132. The edge $26^{5'}$ extends up to the leg 130, which extends radially outwardly a substantial distance from the distal end 138 of the cautery component $36^{5'}$, to effectively shield the same. Thus, the leg 130 is strategically situated to allow repositioning of tissue within a body cavity while additionally affording the electrically insulating barrier between the tissue and the cautery component $36^{5'}$.

Figure 23:
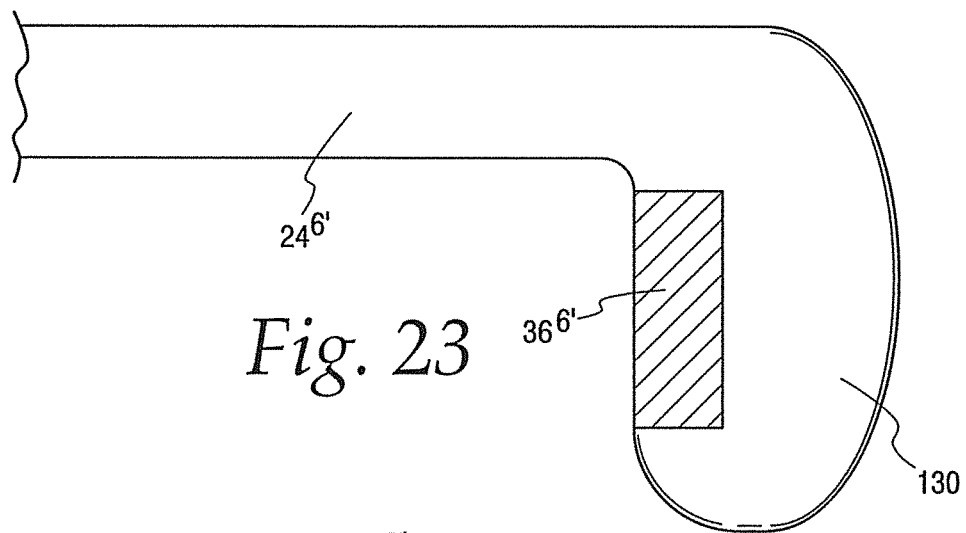
FIG. 23 is a view as in FIG. 22 of a further modified form of medical instrument, according to the invention.
Figure 24:
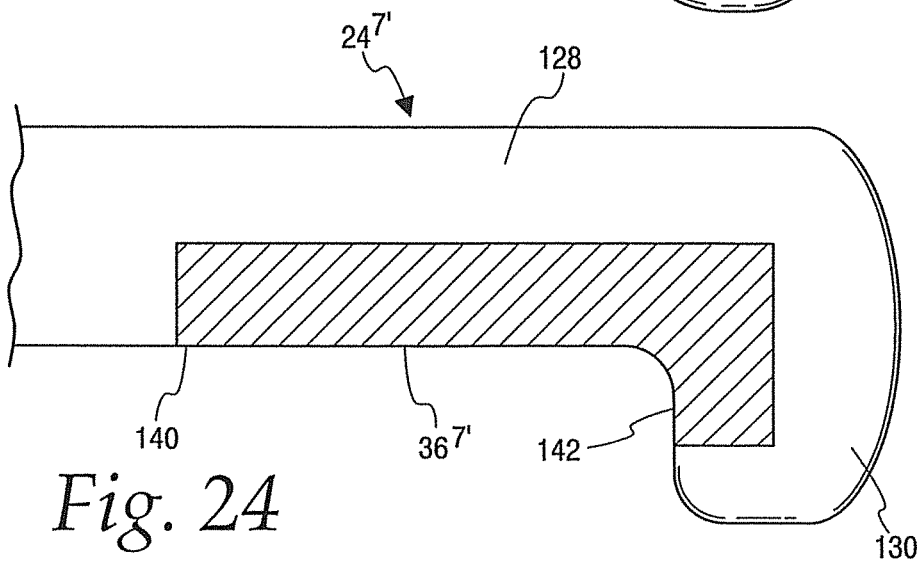
FIG. 24 is a view as in FIG. 23 of a further modified form of medical instrument, according to the invention.

FIGS. 23 and 24 show tips $24^{6'}$, $24^{7'}$, respectively, that are variations of the tip $24^{5'}$. The only difference in each is the configuration of the cautery component.

In FIG. 23, the cautery component $36^{6'}$ is located on the leg 130, whereas on the tip $24^{7'}$, the cautery component $36^{7'}$ essentially combines the configurations of the cautery components $36^{5'}$, $36^{6'}$ to wrap around both legs 128, 130. Accordingly, the cautery component $36^{7'}$ is made up of separate straight edge lengths 140, 142 that are angled with respect to each other.

In FIG. 25, a further form of medical instrument shown at $10^{8'}$ that has a tip at $24^{8'}$ that defines by itself, or in conjunction with a part of an elongate frame $12^{8'}$, an overall "J" shape.

The "J" shape is defined by a base 144 and spaced long and short legs 146, 148, respectively. The base 144 has an exposed surface 149 with a convexly curved distalmost part thereon at 150 defining the leading free end of a tip $24^{8'}$ on the medical instrument $10^{8'}$. The insulating material is provided between the surface part 150 and cautery component $36^{8'}$. In this embodiment, the cautery component $36^{8'}$ is provided on the base 144. The cautery component itself may be extended, or additional cautery components may be provided, to form a cutting edge on one or both of the legs 146, 148.

With each of the embodiments in FIGS. 21-25, the exposed surfaces on each of the tips $24^{4'}$-$24^{8'}$ can be made substantially entirely, or strategically, from insulating material to control collateral damage due to current flow to the tissue in the region at which cauterization is carried out. The insulating material also allows the various medical instruments to be repositioned to move tissue within a cavity, as upon introduction of the instrument and/or to gain access to a particular site, while the cauterization component is energized without inflicting any appreciable damage.

With the above-described structures, a method can be carried out as shown in flow diagram form in FIG. 27.

As shown in block 152, a medical instrument is provided, as described above. As shown at block 154, the medical instrument is repositioned so that the distal end thereof is moved up to and into contact with a human body part at a cutting location. As shown at block 156, at least one cautery component is operated to alter the contacted human body part at the cutting location.

Preferably, the contact with tissue, other than that to be treated, occurs primarily through the insulating material, at least while the one or more cautery components are energized.

The foregoing disclosure of specific embodiments is intended to be illustrative of the broad concepts comprehended by the invention.

The invention claimed is:

1. A medical instrument comprising:
an elongate frame with proximal and distal ends spaced in a lengthwise direction along a central axis of the frame;
an operating assembly at a proximal region of the frame; and
a working assembly at a distal region of the frame,
the working assembly comprising a tip with a leading free end to be engaged with a human body at an operation site,
the working assembly comprising at least one cautery component that: a) contacts a human body part at the cutting location; and b) is operable to generate a current that alters a contacted portion of the human body part at the cutting location,
wherein an insulating material that is not electrically conductive is located at least one of: i) at the leading free end; and ii) between the at least one cautery component and the leading free end so that current does not conduct from the at least one cautery component to the leading free end to human body tissue during a medical procedure,
wherein the tip defines in conjunction with a part of the elongate frame a "J" shape.

2. The medical instrument according to claim 1 wherein the insulating material is at the leading free end.

3. The medical instrument according to claim 1 wherein the elongate frame and tip are substantially straight from a proximal region of the elongate frame fully to the leading free end.

4. The medical instrument according to claim 1 wherein the tip defines in conjunction with a part of the elongate frame an "L" shape.

5. The medical instrument according to claim 1 wherein the "J" shape is defined by a base and spaced legs and the base has an exposed surface defining a distalmost part of the medical instrument and insulating material that is not electrically conductive is located at least one of: a) at the exposed surface on the base; and b) between the at least one cautery component and the exposed surface on the base so that current does not conduct from the at least one cautery component to the exposed surface on the base to human body tissue during a medical procedure.

6. The medical instrument according to claim 1 wherein the tip has an orientation that is at all times fixed.

7. The medical instrument according to claim 1 wherein the tip can be selectively reoriented relative to the frame through the working assembly.

8. The medical instrument according to claim 1 wherein the at least one cautery component has an edge that engages the human body part at the cutting location and the edge is one of: a) substantially straight; and b) defined by two substantially straight lengths that are angled with respect to each other.

9. The medical instrument according to claim 8 wherein the insulating material is one of: a) a plastic; and b) a non-metal material.

10. The medical instrument according to claim 1 wherein the at least one cautery component comprises an edge on a cylindrical portion of the medical instrument and the insulating material is provided on the cylindrical portion of the medical instrument at a location diametrically opposite to the edge.

11. The medical instrument according to claim 1 wherein the tip has an exposed outer surface area, the at least one cautery component comprises a blade with an exposed portion making up a part of the exposed surface area and substantially the entirety of the exposed surface area, with the exception of the exposed portion of the blade, is made from the insulating material.

12. The medical instrument according to claim 1 wherein the leading free end is convexly curved.

13. The medical instrument according to claim 4 wherein the "L" shape is defined by angled legs, one of the angled legs having a convex surface defining a distalmost part of the medical instrument.

14. The medical instrument according to claim 3 wherein the leading free end is convexly curved.

15. The medical instrument according to claim 5 wherein the at least one cautery component comprises a blade that is provided on the base of the "J".

16. The medical instrument according to claim 1 wherein the at least one cautery component comprises a blade and the insulating material extends radially outwardly from the central axis of the frame beyond the blade.

17. A method of performing a surgical procedure, the method comprising the steps of:
providing a medical instrument as recited in claim 1;
repositioning the medical instrument so that the distal end of the medical instrument is moved up to and into contact with a human body part at a cutting location; and
operating the at least one cautery component to alter the contacted human body part at the cutting location through the generated current.

18. The method of performing a surgical procedure according to claim 17 further comprising the step of repositioning a portion of the contacted human body part by bearing the insulating material against the portion of the human body part.

19. The medical instrument according to claim 1 wherein the surgical procedure is carried out while maintaining the tip at all times in a fixed orientation.

20. A method of performing a surgical procedure, the method comprising the steps of:
a) providing a medical instrument comprising:
an elongate frame with proximal and distal ends spaced in a lengthwise direction along a central axis of the frame;

an operating assembly at a proximal region of the frame; and a working assembly at a distal region of the frame, the working assembly comprising a tip with a leading free end to be engaged with a human body at an operation site, the working assembly comprising at least one cautery component that: a) contacts a human body part at the cutting location; and b) is operable to generate a current that alters a contacted portion of the human body part at the cutting location, wherein an insulating material that is not electrically conductive is located at least one of: i) at the leading free end; and ii) between the at least one cautery component and the leading free end so that current does not conduct from the at least one cautery component to the leading free end to human body tissue during a medical procedure;

b) repositioning the medical instrument so that the distal end of the medical instrument is moved up to and into contact with a human body part at a cutting location; and c) operating the at least one cautery component to alter the contacted human body part at the cutting location through the generated current, wherein the step of repositioning the medical instrument comprises repositioning the medical instrument so that the human body part placed at the cutting location contacts electrically conductive material only on the at least one cautery component as the at least one cautery component is operated.

21. A medical instrument comprising:

an elongate frame with proximal and distal ends spaced in a lengthwise direction along a central axis of the frame;

an operating assembly at a proximal region of the frame; and a working assembly at a distal region of the frame, the working assembly comprising a tip with a leading free end to be engaged with a human body at an operation site, the working assembly comprising at least one cautery component that: a) contacts a human body part at the cutting location; and b) is operable to generate a current that alters a contacted portion of the human body part at the cutting location, wherein an insulating material that is not electrically conductive is located at least one of: i) at the leading free end; and ii) between the at least one cautery component and the leading free end so that current does not conduct from the at least one cautery component to the leading free end to human body tissue during a medical procedure, wherein the insulating material is at the leading free end.

22. A medical instrument comprising:

an elongate frame with proximal and distal ends spaced in a lengthwise direction along a central axis of the frame;

an operating assembly at a proximal region of the frame; and a working assembly at a distal region of the frame, the working assembly comprising a tip with a leading free end to be engaged with a human body at an operation site, the working assembly comprising at least one cautery component that: a) contacts a human body part at the cutting location; and b) is operable to generate a current that alters a contacted portion of the human body part at the cutting location, wherein an insulating material that is not electrically conductive is located at least one of: i) at the leading free end; and ii) between the at least one cautery component and the leading free end so that current does not conduct from the at least one cautery component to the leading free end to human body tissue during a medical procedure, wherein the tip defines in conjunction with a part of the elongate frame an "L" shape.

23. A medical instrument comprising:

an elongate frame with proximal and distal ends spaced in a lengthwise direction along a central axis of the frame;

an operating assembly at a proximal region of the frame; and a working assembly at a distal region of the frame, the working assembly comprising a tip with a leading free end to be engaged with a human body at an operation site, the working assembly comprising at least one cautery component that: a) contacts a human body part at the cutting location; and b) is operable to generate a current that alters a contacted portion of the human body part at the cutting location, wherein an insulating material that is not electrically conductive is located at least one of: i) at the leading free end; and ii) between the at least one cautery component and the leading free end so that current does not conduct from the at least one cautery component to the leading free end to human body tissue during a medical procedure, wherein the at least one cautery component comprises an edge on a cylindrical portion of the medical instrument and the insulating material is provided on the cylindrical portion of the medical instrument at a location diametrically opposite to the edge.

24. A medical instrument comprising:

an elongate frame with proximal and distal ends spaced in a lengthwise direction along a central axis of the frame;

an operating assembly at a proximal region of the frame; and a working assembly at a distal region of the frame, the working assembly comprising a tip with a leading free end to be engaged with a human body at an operation site, the working assembly comprising at least one cautery component that: a) contacts a human body part at the cutting location; and b) is operable to generate a current that alters a contacted portion of the human body part at the cutting location, wherein an insulating material that is not electrically conductive is located at least one of: i) at the leading free end; and ii) between the at least one cautery component and the leading free end so that current does not conduct from the at least one cautery component to the leading free end to human body tissue during a medical procedure, wherein the tip has an exposed outer surface area, the at least one cautery component comprises a blade with an exposed portion making up a part of the exposed surface area and substantially the entirety of the exposed surface area, with the exception of the exposed portion of the blade, is made from the insulating material.

* * * * *